(12) United States Patent
Cottrell

(10) Patent No.: US 7,385,097 B1
(45) Date of Patent: Jun. 10, 2008

(54) PROCESS FOR THE PURIFICATION OF A DIOLEFIN HYDROCARBON STREAM

(75) Inventor: Paul R. Cottrell, Arlington Heights, IL (US)

(73) Assignee: UOP LLC, Des Plaines, IL (US)

(*) Notice: Subject to any disclaimer, the term of this patent is extended or adjusted under 35 U.S.C. 154(b) by 437 days.

(21) Appl. No.: 11/170,510

(22) Filed: Jun. 29, 2005

(51) Int. Cl.
*C07C 7/167* (2006.01)

(52) U.S. Cl. .................................... 585/262; 585/259

(58) Field of Classification Search ............... 585/262, 585/259
See application file for complete search history.

(56) References Cited

U.S. PATENT DOCUMENTS 3,076,858 A    2/1963   Frevel et al. ............... 260/677

*Primary Examiner*—Thuan Dinh Dang
(74) *Attorney, Agent, or Firm*—Arthur E. Gooding

(57) ABSTRACT

A process for the purification of a diolefin hydrocarbon stream containing acetylene and sulfur compounds.

18 Claims, 1 Drawing Sheet

US 7,385,097 B1

PROCESS FOR THE PURIFICATION OF A DIOLEFIN HYDROCARBON STREAM

BACKGROUND OF THE INVENTION

This invention relates to a process for the purification of a diolefin hydrocarbon stream containing trace quantities of acetylene and sulfur compounds and the cyclic regeneration of an at least partially spent selective hydrogenation catalyst containing at least one metal. More particularly the present invention relates to methods of reclaiming catalysts which have become deactivated and to the catalytic reduction of acetylenic bonds in the presence of dienes without substantial destruction of the diene compounds.

The selective hydrogenation of the acetylene compounds is generally conducted in the presence of a selective hydrogenation catalyst and hydrogenation and conducted at an elevated pressure and temperature. Such selective hydrogenation catalysts are well known in the art and include, for example, a catalyst containing copper metal associated with one or more activator metals impregnated on an alumina support. During the acetylene hydrogenation, polymers are formed and deposited on the catalyst thereby reducing the activity of the catalyst. One method of regenerating spent or partially spent catalyst is to perform a controlled carbon burn with oxygen and subsequent metal reduction with hydrogen to remove catalyst contaminants which are formed as an undesirable by-product of the acetylene hydrogenation. The carbon burn regeneration technique necessarily requires that the reaction zone contain spent catalyst be taken off line and that ancillary regeneration equipment be provided.

Another alternative technique for regenerating spent or partially spent catalyst is to contact such catalyst with hydrogen and a polymer solvent in order to restore at least a portion of the fresh catalyst activity.

Some of the diolefin hydrocarbon stream containing trace quantities of acetylenes also contain trace quantities of sulfur compounds. These diolefin hydrocarbon feedstocks produce a deactivated catalyst which is not satisfactorily regenerated via the known and conventional regeneration techniques.

INFORMATION DISCLOSURE

U.S. Pat. No. 3,076,858 (Frevel et al.) discloses a process for the selective hydrogenation of acetylenic hydrocarbons in a $C_4$ mixture. A catalyst consisting of 99.9 weight percent copper and 0.1 weight percent nickel on a gamma-alumina carrier is disclosed for use therein. Contaminated or poisoned catalyst can be regenerated by passing air or a mixture of steam and air over the catalysts while they are heated at temperatures between 400° and 600° C.

Although a wide variety of process flow schemes, operating conditions, catalysts and regeneration techniques have been used in commercial activities, there is always a demand for new selective hydrotreating processes which provide lower costs, higher selectivity, better catalyst regeneration and longer on-stream operation.

BRIEF SUMMARY OF THE INVENTION

The present invention is a selective acetylene hydrogenation process which is able to process a diolefin hydrocarbon feedstock containing trace quantities of acetylene and sulfur compounds to produce a high quality diolefin hydrocarbon having extremely low levels of acetylene over an extended period because of the ability to readily regenerate catalyst contained in an off-line reaction zone while continuing to operate an on-line selective hydrogenation reaction zone. The spent or partially spent catalyst is contacted with a hot hydrogen stream to chemically reduce at least a portion of the metal sulfide contained in the spent catalyst and subsequently contacted with an oxygen containing gaseous stream to reduce the polymer content thereof and to thereby increase the hydrogenation activity of the catalyst.

The present invention is able to maintain the high activity of the selective hydrogenation catalyst by discontinuing the flow of diolefinic hydrocarbon feedstock to at least one off-line hydrogenation reaction zone and contacting the at least partially spent catalyst with a hot hydrogen stream to chemically reduce at least a portion of the metal sulfide resulting from the processing of a feedstock containing trace quantities of sulfur compounds. The resulting catalyst having been treated with a hot hydrogen stream is subsequently contacted with an oxygen containing gaseous stream to thereby reduce at least a portion of the polymer content of the catalyst and to thereby increase and restore the hydrogenation activity.

BRIEF DESCRIPTION OF THE DRAWING

The drawing is a simplified process flow diagram of a preferred embodiment of the present invention. The drawing is intended to be schematically illustrative of the present invention and not to be a limitation thereof.

DETAILED DESCRIPTION OF THE INVENTION

Figure 1:
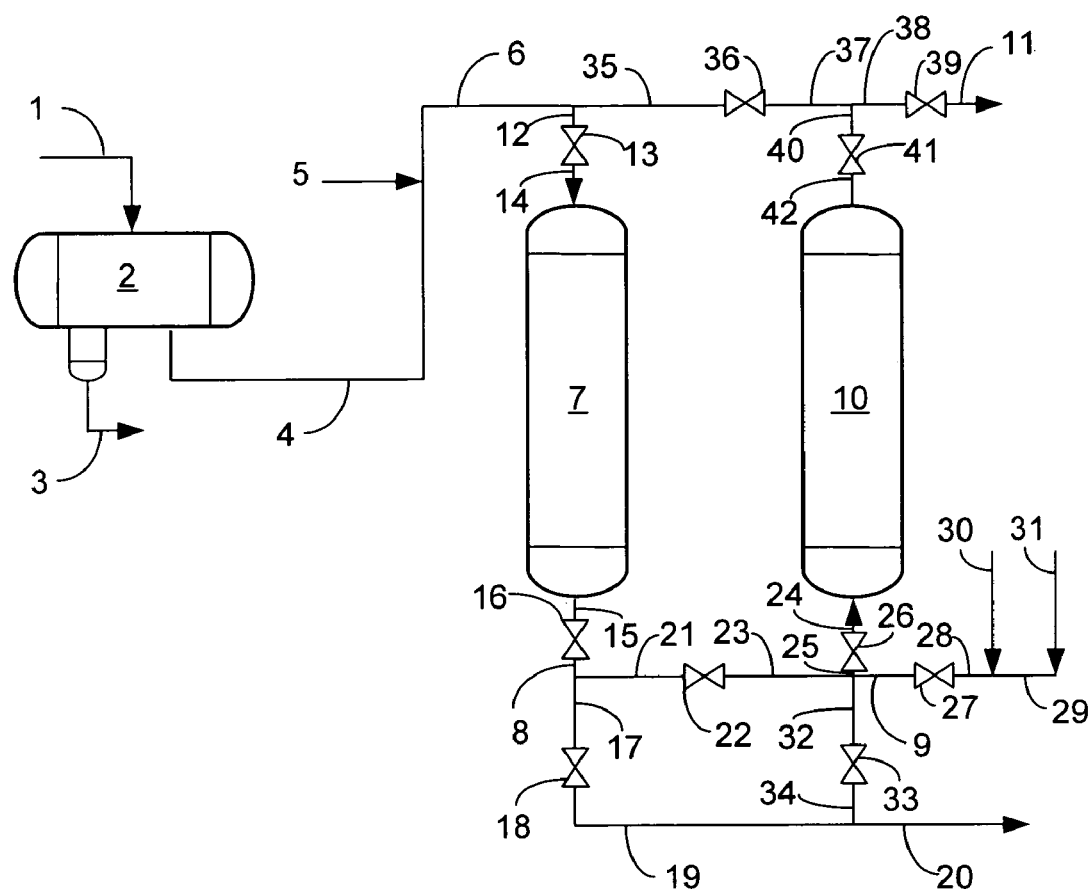

In accordance with the process of the present invention, the process is particularly suitable and capable of reducing the concentration of acetylene in a diolefin hydrocarbon stream containing trace quantities of acetylene and sulfur compounds. Traditional olefinic feedstocks preferably contain little if any sulfur compounds because of upstream preparation or sulfur removal which is conducted prior to introducing the diolefinic feedstock into a selective hydrogenation process. The removal of sulfur compounds such as hydrogen sulfide usually performed in a sulfur adsorbent bed. However, for a variety of reasons if the diolefinic feedstock cannot be maintained with essentially no sulfur compound contaminants due to inefficient or faulty sulfur removal, the process of the present invention is able to successfully process such feedstock. Trace quantities of acetylene and sulfur are preferably expected to be in the range from about 0.5 to about 5 weight percent and from about 0.5 to about 50 wppm, respectively.

Any suitable catalyst which is capable of selectively hydrogenating acetylene in a diolefinic feed stream may be used in the present invention. A particularly preferred selective hydrogenation catalyst comprise copper and at least one other metal such as titanium, vanadium, chrome, manganese, cobalt, nickel, zinc, molybdenum, and cadmium or mixtures thereof. The metals are preferably supported on inorganic oxide supports such as silica and alumina, for example.

The supported catalyst is ordinarily prepared by immersing the supports in an aqueous solution of the salts of the metals of which the catalyst is to be composed, then removing and drying the supports, heating in air to convert the metal salts into the corresponding oxides, and reducing the latter with hydrogen. The step of heating or calcining to convert the metal salts to oxides is usually accomplished at a temperature from about 350° to about 550° C. Reduction of the metal oxides is preferably conducted at a temperature below 550° C. A preferred selective hydrogenation catalyst comprises copper and nickel supported on alumina.

Preferred feedstocks for the present invention are 1,3-butadiene-containing hydrocarbon streams and $C_4$ or $C_3$ hydrocarbons containing 1,3-diolefins, 1,2-diolefins and acetylenes. Any other feedstocks containing diolefin hydrocarbons and trace quantities of acetylene and sulfur compounds may also be used as feedstocks.

In accordance with the present invention, the selected diolefin feedstock containing acetylene and sulfur compounds is introduced along with hydrogen into an on-line selective hydrogenation reaction zone operating at selective hydrogenation conditions and containing a selective hydrogenation catalyst to produce an improved diolefin stream having a reduced concentration of acetylene compounds. The selective hydrogenation conditions will depend upon the selected diolefin feed and may preferably be selected from a pressure from about 1480 kPa (200 psig) to about 3550 kPa (500 psig) and a temperature from about 32° C. (90° F.) to about 83° C. (180° F.).

In an alternating fashion, an off-line reaction zone containing selective hydrogenation catalyst, either spent or partially spent is preferably first contacted with a hot, hydrogen stream to reduce the level of sulfur contained on the spent catalyst at metal reducing conditions preferably including a pressure from about 197 kPa (14 psig) to about 1480 kPa (200 psig), a temperature from about 50° C. (122° F.) to about 250° C. (482° F.) and a gas hourly space velocity from about 180 $hr^{-1}$ to about 500 $hr^{-1}$. The sulfur level on the spent catalyst is preferably reduced by at least 90%. After the spent catalyst has been contacted with the hot hydrogen to remove sulfur therefrom, the spent catalyst is contacted with an oxygen containing gaseous stream to combust carbonaceous deposits contained on the catalyst and thereby regenerate the catalyst. The combustion of the carbonaceous deposits contained on the catalyst is preferably conducted at conditions which preferably include a pressure from about 197 kPa (14 psig) to about 1480 kPa (200 psig), a temperature from about 250° C. (482° F.) to about 500° C. (932° F.) and a gas hourly space velocity from about 2000 $hr^{-1}$ to about 7000 $hr^{-1}$. The oxygen level or concentration in the oxygen containing contacting stream is preferably controlled to maintain a steady, even combustion to prevent any thermal damage to the catalyst. Preferably, the carbonaceous deposits are reduced to a level of essentially nil. The resulting regenerated catalyst is preferably reduced with a hot hydrogen-rich gaseous stream to reduce the metal on the catalyst to an elemental state. This reduction is preferably conducted at a temperature from about 200° C. (392° F.) to about 300° C. (572° F.).

The selective hydrogenation catalyst may be any suitable known catalyst as noted and described hereinabove and may contain one or more beds of the same or different selective hydrogenation catalyst. The selective hydrogenation catalysts contemplated for use in the process of the present invention include any support types, sizes and shapes, for example, spheres, cylinders, tri-lobes, quadra-lobes and rings. The process of the present invention is not limited by the type of hydrogenation catalyst and any suitable selective hydrogenation catalyst is contemplated for use therein.

DETAILED DESCRIPTION OF THE DRAWING

In the drawing, the process of the present invention is illustrated by means of a simplified schematic flow diagram in which such details as pumps, instrumentation, heat-exchange and heat-recovery circuits, compressors and similar hardware have been deleted as being non-essential to an understanding of the techniques involved. The use of such miscellaneous equipment is well within the purview of one skilled in the art.

With reference now to the drawing, a feed stream comprising butadiene, acetylene and sulfur, and steam condensate is introduced into the process via line 1 and is passed into feed surge drum 2. The acetylene concentration is about 1 weight percent acetylene and about 10 wppm sulfur. The concentration of steam condensate is dependent upon the upstream process and is preferably less than about 5 weight percent. A condensate stream is removed from feed surge drum 2 via line 3 and recovered. A stream containing butadiene, acetylene and sulfur is removed from feed surge drum 2 via line 4 and is admixed with a hydrogen-rich gaseous stream provided via line 5 and the resulting admixture is introduced into on-line selective hydrogenation zone 7 via line 6, line 12, valve 13 and line 14. On-line selective hydrogenation zone 7 is preferably operated in a downflow manner. An effluent stream containing butadiene and having a reduced concentration of acetylene compounds is removed from on-line selective hydrogenation zone 7 via line 15, valve 16, line 8, line 17, valve 18, line 19, and line 20 and recovered for further purification and subsequent use. Alternatively, the resulting admixture is transported via line 6, line 35, valve 36, line 37, line 40, valve 41, line 42 and introduced into selective hydrogenation zone 10. An effluent stream containing butadiene and having a reduced concentration of acetylene compounds is removed from selective hydrogenation zone 10 via line 24, valve 26, line 25, line 32, valve 33, line 34 and line 20 and recovered for further purification and subsequent use.

A stream of hot hydrogen carried via line 30, line 28, valve 27, line 9, line 25, valve 26 and line 24 is introduced into off-line selective hydrogenation zone 10, which is spent and deactivated, to remove sulfur. A hydrogen stream containing sulfur compounds is removed from off-line selective hydrogenation zone 10, preferably in an upflow manner, via line 42, valve 41, line 40, line 38, valve 39 and line 11, and recovered. After the hot hydrogen strip as previously described is completed, an oxygen containing gaseous stream is introduced via line 31, line 29, line 28, valve 27, line 9, line 25, valve 26 and line 24 into off-line selective hydrogenation zone 10 to combust the polymer contained thereon with oxygen. A resulting stream containing oxidized polymer is removed from off-line selective hydrogenation zone 10 via line 42, valve 41, line 40, line 38, valve 39 and line 11, and recovered.

Alternatively, a stream of hot-hydrogen carried via line 30, line 28, valve 27, line 9, line 23, valve 22, line 21, line 8, valve 16 and line 15 is introduced into selective hydrogenation zone 7. A hydrogen stream containing sulfur compounds is removed from selective hydrogenation zone 7, preferably in an upflow manner, via line 14, valve 13, line 12, line 35, valve 36, line 37, line 38, valve 39 and line 11, and recovered. After the hot hydrogen strip as previously described is completed, an oxygen-containing gaseous stream is introduced via line 31, line 29, line 28, valve 27, line 9, line 23, valve 22, line 21, line 8, valve 16 and line 15 into selective hydrogenation zone 7 to combust the polymer contained therein with oxygen. A resulting stream containing oxidized polymer is removed from selective hydrogenation zone 7 via line 14, valve 13, line 12, line 35, valve 36, line 37, line 38, valve 39 and line 11, and recovered.

Off-line selective hydrogenation zone 10, now regenerated, is then placed in service for the selective hydrogenation of the feedstock as described hereinabove. After in-line selective hydrogenation zone 7 is spent and deactivated, it in turn is regenerated.

The process of the present invention is further demonstrated by the following example. This example is, however, not presented to unduly limit the process of this invention, but to further illustrate the advantage of the hereinabove-described embodiment.

EXAMPLE

A selective hydrogenation reaction zone containing a selective hydrogenation catalyst containing copper and nickel and supported on alumina was charged with a raw butadiene stream containing about 0.8 weight percent acetylene and about 4 weight ppm sulfur. The reaction was operated at a pressure of about 2.8 MPa (290 psig) and a temperature of about 45° C. (113° F.). The resulting selective hydrogenated feedstock contained about 3 wppm acetylene. After about eleven days on stream, the catalyst became spent and the selective hydrogenation zone was taken off-line. The previous regeneration of this spent catalyst was conducted with only a steam and air regeneration.

In accordance with the present invention, the spent catalyst described hereinabove was purged with a hot hydrogen stream maintained at a temperature of about 150° C. (300° F.) for about 50 hours to remove more than about 90% of the sulfur from the catalyst. After the completion of the hot hydrogen treatment, the catalyst was contacted with an oxygen containing gaseous stream maintained at a temperature of about 325° C. (617° F.) to combust essentially all of the polymer from the catalyst.

The resulting regenerated catalyst was reduced with a hydrogen-rich gaseous stream to reduce the metal on the catalyst to an elemental state. Then the catalyst bed was returned to selective hydrogenation service as described hereinabove. The catalyst was able to perform satisfactorily and to selectively hydrogenate acetylene to a product level of about 3 wppm acetylene for a total of about 31 days before the next catalyst regeneration was required. Therefore, it can be noted that the selective hydrogenation catalyst regeneration in accordance with the present invention increased the run length from about 11 days to about 31 days. This increase in run length affords a large economic benefit in a commercial process unit.

The foregoing description, drawing and example clearly illustrate the advantages encompassed by the process of the present invention and the benefits to be afforded with the use thereof.

What is claimed is:

1. A process for the purification of a diolefin hydrocarbon stream containing acetylene and sulfur compounds and the cyclic regeneration of an at least partially spent selective hydrogenation catalyst containing at least one metal which process comprises:
   (a) introducing the diolefin hydrocarbon stream containing acetylene and sulfur compounds, and elemental hydrogen into a selective hydrogenation zone containing selective hydrogenation catalyst to selectively hydrogenate at least a portion of the acetylene and to produce an at least partially spent selective hydrogenation catalyst containing metal sulfide and polymer;
   (b) passing the resulting effluent from the selective hydrogenation zone in step (a) to recover a diolefinic hydrocarbon stream having a reduced concentration of acetylene;
   (c) contacting the at least partially spent selective hydrogenation catalyst containing metal sulfide in the selective hydrogenation zone with a hot hydrogen stream to chemically reduce at least a portion of the metal sulfide;
   (d) contacting the selective hydrogenation catalyst from step (c) with an oxygen containing gaseous stream to combust the polymer content therefrom and to thereby increase hydrogenation activity; and
   (e) introducing the diolefin hydrocarbon stream containing acetylene and sulfur compounds, and elemental hydrogen into the selective hydrogenation zone after contact with the oxygen containing gaseous stream.

2. The process of claim 1 wherein the diolefin hydrocarbon stream comprises butadiene.

3. The process of claim 1 wherein the selective hydrogenation zone contains a catalyst comprising copper metal.

4. The process of claim 1 wherein the selective hydrogenation zone is operated in step (a) at conditions including a pressure from about 1.4 MPa (200 psig) to about 3.5 MPa (500 psig) and a temperature from about 32° C. (90° F.) to about 83° C. (180° F.).

5. The process of claim 1 wherein the contacting in step (c) is conducted at conditions including a pressure from about 197 kPa (14 psig) to about 1480 kPa (200 psig), a temperature from about 50° C. (122° F.) to about 250° C. (482° F.) and a gas hourly space velocity (GHSV) from about 180 $hr^{-1}$ to about 500 $hr^{-1}$.

6. The process of claim 1 wherein the diolefin hydrocarbon stream comprises a compound selected from a group of diolefins containing from about 3 to about 5 carbon atoms.

7. The process of claim 1 wherein the selective hydrogenation catalyst comprises copper and alumina.

8. The process of claim 1 wherein the contacting in step (d) is conducted at conditions including a pressure from about 197 kPa (14 psig) to about 1480 kPa (200 psig), a temperature from about 250° C. (482° F.) to about 500° C. (932° F.) and a gas hourly space velocity (GHSV) from about 2000 $hr^{-1}$ to about 7000 $hr^{-1}$.

9. A process for the purification of a diolefin hydrocarbon stream containing acetylene and sulfur compounds and the cyclic regeneration of an at least partially spent selective hydrogenation catalyst containing at least one metal which process comprises:
   (a) introducing the diolefin hydrocarbon stream containing acetylene compounds and sulfur compounds, and elemental hydrogen into a selective hydrogenation zone containing selective hydrogenation catalyst to produce an at least partially spent selective hydrogenation catalyst containing metal sulfide;
   (b) passing the resulting effluent from the selective hydrogenation zone in step (a) to recover a diolefinic hydrocarbon stream having a reduced concentration of acetylene;
   (c) contacting the at least partially spent selective hydrogenation catalyst containing metal sulfide in the selective hydrogenation zone with a hot hydrogen stream operated at a pressure from about 197 kPa (14 psig) to about 1480 kPa (200 psig), a temperature from about 50° C. (122° F.) to about 250° C. (482° F.) and a gas hourly space velocity from about 180 $hr^{-1}$ to about 500 $hr^{-1}$ to chemically reduce at least a portion of the metal sulfide;

(d) contacting the selective hydrogenation catalyst from step (c) with an oxygen containing gaseous stream to combust the polymer content therefrom and to thereby increase hydrogenation activity; and (e) introducing the diolefin hydrocarbon stream containing acetylene and sulfur compounds, and elemental hydrogen into the selective hydrogenation zone after contact with the oxygen containing gaseous stream.

10. The process of claim 9 wherein the diolefin hydrocarbon stream comprises butadiene.

11. The process of claim 9 wherein the selective hydrogenation zone contains a catalyst comprising copper metal.

12. The process of claim 9 wherein the diolefin hydrocarbon stream comprises a compound selected from a group of diolefins containing from about 3 to about 5 carbon atoms.

13. The process of claim 9 wherein the selective hydrogenation catalyst comprises copper and alumina.

14. A process for the purification of a butadiene hydrocarbon stream containing acetylene and sulfur compounds and the cyclic regeneration of an at least partially spent selective hydrogenation catalyst containing copper and alumina which process comprises:

(a) introducing the diolefin hydrocarbon stream containing acetylene compounds and sulfur compounds, and elemental hydrogen into a selective hydrogenation zone containing a catalyst comprising copper and alumina to selectively hydrogenate at least a portion of the acetylene and to produce an at least partially spent catalyst containing copper sulfide and polymer;

(b) passing the resulting effluent from the selective hydrogenation zone in step (a) to recover a butadiene stream having a reduced concentration of acetylene;

(c) contacting the at least partially spent catalyst containing copper sulfide in the selective hydrogenation zone with a hot hydrogen stream to chemically reduce at least a portion of the copper sulfide;

(d) contacting the catalyst from step (c) with an oxygen containing gaseous stream to combust the polymer content therefrom and to thereby increase hydrogenation activity;

(e) contacting the selective hydrogenation catalyst from step (d) with a hot hydrogen stream to chemically reduce at least a portion of the metal; and (f) introducing the butadiene hydrocarbon stream containing acetylene and sulfur compounds, and elemental hydrogen into the selective hydrogenation zone after contact with the hot hydrogen stream in step (e).

15. The process of claim 14 wherein the selective hydrogenation zone is operated in step (a) at conditions including a pressure from about 1.4 MPa (200 psig) to about 3.5 MPa (500 psig) and a temperature from about 32° C. (90° F.) to about 83° C. (180° F.).

16. The process of claim 14 wherein the contacting in step (c) is conducted at conditions including a pressure from about 197 kPa (14 psig) to about 1480 kPa (200 psig), a temperature from about 50° C. (122° F.) to about 250° C. (482° F.) and a gas hourly space velocity (GHSV) from about 180 $hr^{-1}$ to about 500 $hr^{-1}$.

17. The process of claim 14 wherein the contacting in step (d) is conducted at conditions including a pressure from about 197 kPa (14 psig) to about 1480 kPa (200 psig), a temperature from about 250° C. (482° F.) to about 500° C. (932° F.) and a gas hourly space velocity (GHSV) from about 2000 $hr^{-1}$ to about 7000 $hr^{-1}$.

18. The process of claim 14 wherein the contacting in step (e) is conducted at conditions including a temperature from about 200° C. (392° F.) to about 300° C. (572° F.).

* * * * *